(12) United States Patent
Vinogradov-Nurenberg et al.

(10) Patent No.: US 10,132,733 B2
(45) Date of Patent: Nov. 20, 2018

(54) UNIVERSAL MECHANICAL TESTER FOR MEASURING FRICTION AND WEAR CHARACTERISTICS OF MATERIALS

(71) Applicants: Michael Vinogradov-Nurenberg, Sunnyvale, CA (US); Vishal Khosla, Fremont, CA (US); Nicholas Doe, San Ramon, CA (US); Gautam Char, Fremont, CA (US)

(72) Inventors: Michael Vinogradov-Nurenberg, Sunnyvale, CA (US); Vishal Khosla, Fremont, CA (US); Nicholas Doe, San Ramon, CA (US); Gautam Char, Fremont, CA (US)

( * ) Notice: Subject to any disclaimer, the term of this patent is extended or adjusted under 35 U.S.C. 154(b) by 0 days.

(21) Appl. No.: 15/838,326

(22) Filed: Dec. 11, 2017

(65) Prior Publication Data

US 2018/0202912 A1    Jul. 19, 2018

Related U.S. Application Data

(60) Provisional application No. 62/438,089, filed on Dec. 22, 2016.

(51) Int. Cl.
| | |
|---|---|
| *G06F 11/30* | (2006.01) |
| *G01N 3/56* | (2006.01) |
| *A47J 37/07* | (2006.01) |
| *A47B 5/04* | (2006.01) |
| *A47B 5/02* | (2006.01) |

(52) U.S. Cl.
CPC ............ *G01N 3/56* (2013.01); *A47J 37/0786* (2013.01); *A47B 5/02* (2013.01); *A47B 5/04* (2013.01); *A47J 2037/0777* (2013.01); *G01N 2203/0676* (2013.01); *G01N 2203/0694* (2013.01)

(58) Field of Classification Search
CPC ........................................................ G01N 3/56
See application file for complete search history.

(56) References Cited

U.S. PATENT DOCUMENTS

| | | | |
|---|---|---|---|
| 5,736,630 | A | 4/1998 | Welner et al. |
| 6,430,520 | B1 * | 8/2002 | Tranquilla ............. G01G 23/10 702/141 |
| 6,615,640 | B2 | 9/2003 | Ahn et al. |
| 7,013,706 | B2 | 3/2006 | Tarumi et al. |
| 9,752,969 | B2 | 9/2017 | Werner et al. |
| 2015/0293001 | A1 * | 10/2015 | Werner .................... G01N 3/56 73/7 |

* cited by examiner

*Primary Examiner* — Phuong Huynh

(57) ABSTRACT

Proposed is a universal mechanical tester for measuring friction and wear characteristics of materials. The tester allows performing multiple test protocols with a single machine. The tester consists of a frame that supports a carriage moveable in a vertical direction, a force sensor assembly attached to the carriage, a positioning stage with a slide and a platform, and a plurality of modular sample stages interchangeably installable on the platform for executing linear and rotary motions of the lower sample relative to the upper sample in various directions and planes. The tester is provided with a set of electronic identification devices for identifying a modular sample stage installed on the platform and the force sensor assembly attached to the carriage.

17 Claims, 9 Drawing Sheets

UNIVERSAL MECHANICAL TESTER FOR MEASURING FRICTION AND WEAR CHARACTERISTICS OF MATERIALS

FIELD OF THE INVENTION

The invention relates in general to the field of tribology and in particular to a universal mechanical tester for measuring friction and wear characteristics of materials.

BACKGROUND OF THE INVENTION

The field of tribology involves the study of friction and wear on materials. In the course of study two or more objects are brought into contact with each other, and a relative motion is started between the two contacting materials for the purpose of measuring the resulting friction forces. Rubbing the two materials against each other results in a damage or wear of the tested objects, and over time a wear track may be created on one or both of the objects; therefore, the wear on one or both of the objects can also be measured.

There exist many different configurations of mechanical testers, each performing a specific dedicated test.

The conventional equipment used for measuring friction and wear is dedicated to a particular test type and a corresponding test configuration. Examples include, without limitation, the configurations referred to in the art as block-on-ring, pin/ball/disk-on-disk, and reciprocating pin/ball on flat. The first represents a configuration where the sample stage includes a horizontal drive shaft rotating around its main axis. A ring specimen is coupled to the shaft for concurrent rotation, and a test block is pushed radially against the edge of the ring with a known force. A friction force and/or a torque imparted on the shaft are measured, from which a coefficient of friction between the block and the specimen material can be calculated based on the known load (i.e., a normal force applied from the block).

Similarly, for the ball-on-disk, pin-on-disk or disk-on-disk test configurations, a disk specimen is mounted horizontally on a vertical rotating shaft in the sample stage. A ball or pin specimen is brought down from above into contact with the spinning face of the disk at a known radial distance from the axis of the shaft, and a known normal force is applied. Thus, a frictional force between the ball or pin and the spinning disk and the resulting wear can be measured. Alternatively, a fixed disk, rather than a ball or pin, is aligned axially with the spinning disk coupled to the stage, and the two are brought into contact with a known force. In this configuration, the friction and wear between the two disks can similarly be measured.

The third exemplary type of test equipment is a reciprocating-type tester. In this configuration, an eccentric crank is used to transfer a rotary motion of the drive shaft to a reciprocating motion in a horizontal plane of the stage where the sample is mounted. By applying a rotational motion to the drive shaft, the horizontal reciprocating motion follows a sinusoidal velocity profile. A test specimen (a flat sample) is mounted on the reciprocating plane, and again a ball or pin specimen is brought into contact with a known normal force. The resulting frictional force is measured, and the coefficient of friction can be calculated. Wear tests can be similarly carried out in a conventional manner.

The fourth exemplary type of test equipment is a fretting tester, which is a variant of a reciprocating-type tester. In this configuration, a linear electro-magnetic actuator is used to enforce a reciprocating motion of the stage where a sample is mounted, usually at a high frequency, with a short amplitude, and in a horizontal plane. By applying a sinusoidal current to the actuator, the horizontal reciprocating motion follows a sinusoidal velocity profile. A test specimen (a flat sample) is mounted on the reciprocating stage, and again a ball or pin specimen is brought into contact with a known normal force. The resulting frictional force is measured, and the coefficient of friction can be calculated. Wear tests can be similarly carried out in a conventional manner.

Each of these tests is normally carried out on a specific, dedicated test machine. Therefore, multiple machines are required, and this is inefficient and therefore undesirable, especially if all available machines are not used simultaneously. In other words, a large area of a laboratory space, which is typically the most expensive space in a production facility, most time will remain unused. Furthermore, specialized test units will incorporate their own dedicated computers, controllers and sensors, the use of which could not be shared with other units of test equipment.

One example of a friction tester is disclosed in U.S. Pat. No. 6,615,640 issued to H. Ahn on Sep. 9, 2003 and relates to a fine friction and wear test apparatus for a plate specimen. The apparatus comprises a fixing unit, a driving unit installed on the fixing unit for fixing and moving a certain plate specimen, a ball specimen support member for rubbing and wearing the plate specimen, a rotation plate position controller fixed on the fixing unit for controlling the position of the ball specimen support member, a ball specimen controller for controlling the ball specimen support member, a controller for detecting the degree of a friction and wear of the plate specimen and controlling each mechanical and circuit part, and a power supply unit for supplying a power to a part which requires a certain power.

U.S. Pat. No. 7,013,706 issued on Mar. 21, 2006 to R. Tarumi discloses a friction force measurement apparatus which measures a friction force between a fixed member fixed on a main body of a magnetic tape drive and a magnetic tape abrading the fixed member is characterized by being equipped with a vibration detector which is joined with the fixed member and a vicinity of the fixed member and detects vibration in abrasion of the magnetic tape with the fixed member, and a calculation device which calculates the friction force between the fixed member and the magnetic tape based on a signal from the vibration detector.

U.S. Pat. No. 6,430,520 issued on Aug. 6, 2002 to M. Tranquilla discloses a dynamic friction measurement apparatus, which includes a load cell, accelerometer, and a computational device for determining the coefficient of friction corrected for inertial forces which otherwise cause an error in the calculation. The calculation device has the functions of simultaneously receiving the signals, conditioning the signals, creating output in digital or analog electrical signals, and storing or providing a value for the coefficient of friction from the dynamic measurements. A method for detecting and processing the coefficient of friction during dynamic condition is also provided.

U.S. Pat. No. 5,736,630 issued on Apr. 7, 1998 to J. Weiner discloses a compact and portable apparatus directed toward measuring the coefficients of both static and sliding friction or slip resistance occurring between two surfaces. Means are provided for determining and recording data to establish such friction accurately, repeatably, and in a form suitable for computer entry and data processing. Improvement over the prior art is provided with respect to mechanical configuration, ease of use, plus the acquisition and analysis of data, particularly for conditions involving wet or damp surfaces. A method is disclosed for essentially automatic determination of coefficient of friction.

Attempts have been made to provide a universal material tester by incorporating replaceable modular sample stages. For example, U.S. Pat. No. 9,752,969 issued on Sep. 5, 2017 to D. Werner et al. describes a universal tester (FIG. 1), wherein alternative modular sample stages are available for use in different test configurations. This tester, which in general is designated by reference numeral 10, has a frame 11, a carriage 12 moveable in a vertical direction indicated by arrow Z, a slide 13 moveable in a horizontal direction indicated by arrow X, a force sensor 14 attached to the slide, a holder 15 for an upper specimen 16, attached to the force sensor, and a base 17 attached to the frame. Each modular sample stage 18, which is attachable to the base in the frame of the unit, includes a support for the lower specimen and a mechanism for moving the lower specimen. The base includes a motor (not shown) permanently attached to the frame and a set of connectors wired to a processor (not shown) that controls the tester operation. Each of the alternative modular sample stages 18 has an adapter, which engages with the shaft of the motor included in the base when the sample stage is attached to the base. The adapter connects the motor shaft with the mechanism for producing a motion of the lower specimen supported by the sample stage. Also, each of the alternative modular sample stages has a set of connectors mating with the connectors in the base and coupled with an identification device mounted in the sample stage. When the sample stage is attached to the base the identification device connects through the mating connectors in the sample stage and in the base to the processor controlling the tester operation. The identification device automatically enables the processor to execute a subset of test operations corresponding to the attached sample stage.

Although this type of test system requires less laboratory space and can be more economically efficient than multiple dedicated testers, nevertheless it has a number of disadvantages, namely: 1) each replaceable alternative modular sample stage is driven by the same common motor, and this cannot provide speed and torque in range that could satisfy optimal conditions for all possible applications; 2) the force sensor assembly with the upper specimen holder is attached to the slide mounted on the vertically movable carriage in such a manner that creates a significant leverage of the force acting on the carriage loading mechanism and causes an unwanted parasitic moment in this mechanism; 3) each force sensor requires a manual software set-up and a system configuration corresponding to the sensor type and range or there must be a dedicated piece of software for each force sensor type and range; 4) the provision of separate environment chambers for measuring friction and wear characteristics of materials at various environmental conditions makes it difficult to set control parameters since such a setting is carried out manually and easily may lead to an error since this setting requires to take into account various control parameters which depend on the chamber volume, working range, etc., and must be individually defined for each chamber model.

SUMMARY OF THE INVENTION

It is an object of the present invention to provide a reliable universal mechanical tester with increased mechanical stability, higher load capacity, and wide range of test parameters, which allows for safe operation without a danger of exceeding load and speed limits at various environmental conditions by automatically detecting and recognizing attached sample motion stages, sensors, environment chambers, automatically retrieving predetermined hardware configuration parameters corresponding to the detected modules, and enabling for execution only the test protocols relevant to the recognized hardware configuration.

The apparatus of the present invention is a universal mechanical tester for measuring friction and wear characteristics of materials that allows for performing multiple test protocols with a single machine. Such result is achieved by using interchangeable modular sample stages, wherein each stage comprises a dedicated actuator optimized to a specific test configuration. The modular sample stages are manually removably coupled to a platform on a positioning stage attached to the base of the instrument, thus allowing for repositioning the modular sample stage with the lower sample relative to the upper loading carriage. Alternative force sensor assemblies with upper specimen holders are manually removably attached to a vertically movable carriage to provide for the upper specimen loading controlled by a central processing unit (CPU) or a computer according to a test protocol. The modular sample stages and the force sensor assemblies include unique identifiers and when coupled to the tester are automatically recognized for activation of the correct software relevant to its configuration and test protocols (scripts). As a result, no extraneous test protocol can be activated erroneously by an operator.

Environment chambers attachable to the modular sample stages and means for controlling and/or measuring the temperature and the humidity of the samples also having unique identifiers, which are used for activation of respective software when being installed. Similar identifiers and respective software are also available for voltage and resistance measurements and for acoustic emission measurements on the materials under test and ensure that only relevant software is enabled, thereby avoiding erroneous script implementations.

Various other advantages will become clear from the description of the invention in the specification that follows and from the novel features particularly pointed out in the appended claims. This invention includes the features hereinafter illustrated in the drawings, fully described in the detailed description of the preferred embodiments and particularly pointed out in the claims, but it is understood that such drawings and description disclose only some of the various ways in which the invention may be practiced.

DESCRIPTION OF THE PREFERRED EMBODIMENT

As used herein, the terms 'specimen' and 'sample' are used interchangeably to refer to the materials tested to determine their wear and friction characteristics. The term 'lower' specimen (or sample) is used to refer to the material coupled to the holders in the modular sample stages of the instrument of the invention. The term 'upper' specimen (or sample) is used to refer to the material coupled to the holder that is attached to the force sensor assembly coupled to the carriage of the instrument to contact and exert a force against the lower specimen and to sense and measure the frictional reaction when a relative motion between upper and lower specimens is initiated or produced by the motion in the sample stage. As described above, the upper specimen may be a pin, a ball, a block or a disk acting on the lower specimen, and a sample motion may be rotational around a horizontal axis, rotational around a vertical axis, or sliding linearly unidirectionally or reciprocatingly along a horizontal direction.

As used herein, the terms 'force sensor assembly' and 'force sensor' are used interchangeably to refer to a sensing device removably attached and coupled to the carriage of the instrument with the purpose of sensing and measuring a force exerted against the lower specimen and the frictional reaction between the upper and the lower specimens.

The universal mechanical tester of the invention was developed to overcome the shortcomings of the apparatus described in U.S. Pat. No. 9,752,969. The improvements lie in the configuration of the modules in relation to the base and frame of the instrument and in the mechanisms used to ensure the correct and safe arrangement and usage of the modules for the desired test procedure. Accordingly, the tester of the invention is not described in details herein other than as necessary to disclose the elements of the invention. The details of the conventional portions of the instrument can be found, for example, in the description of the instrument disclosed in the aforementioned US Patent, which for that purpose is herein incorporated by reference in its entirety.

Figure 1:
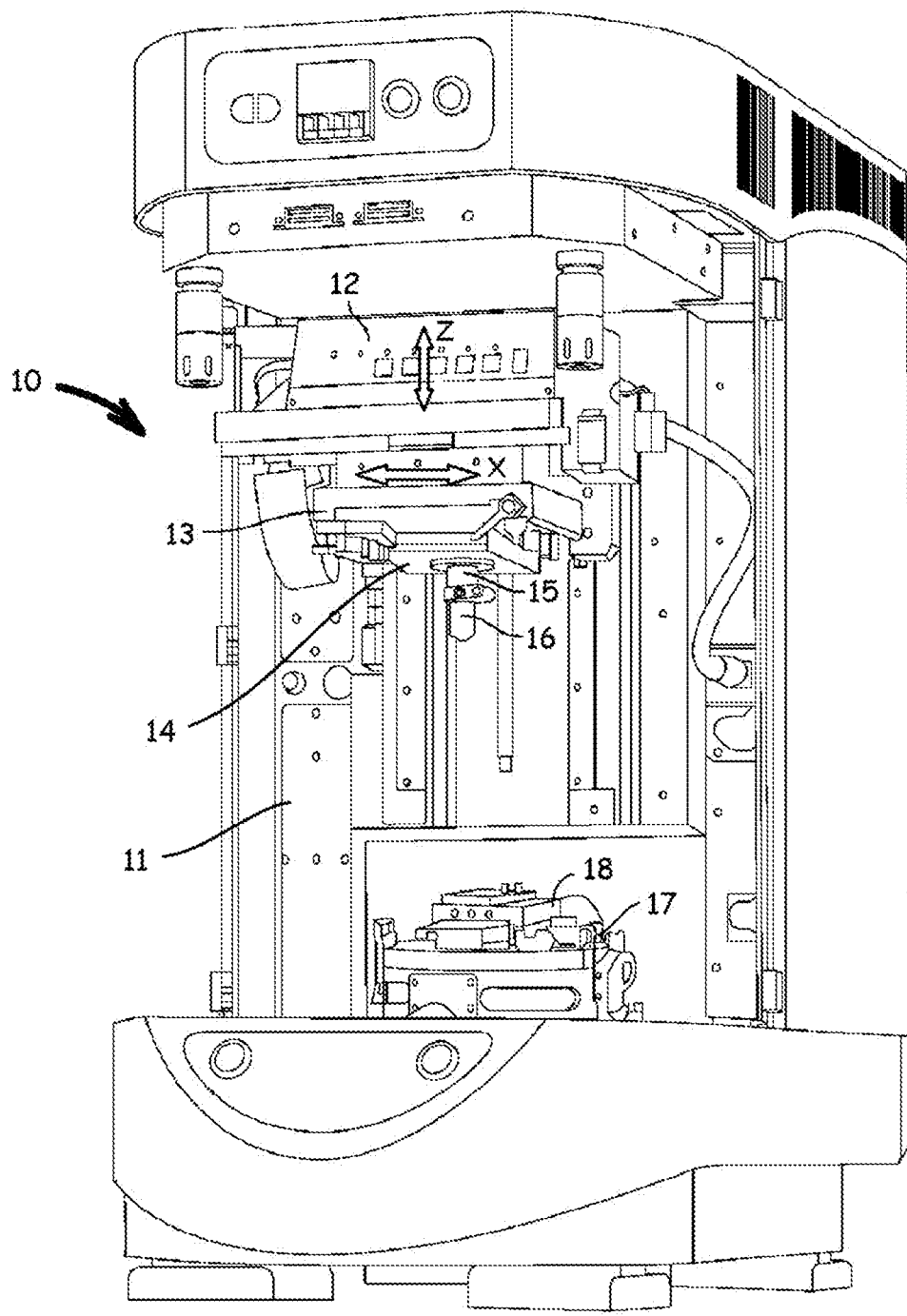
FIG. 1 is a three-dimensional front view of a known test instrument for measuring friction and wear characteristics of the materials.
Figure 2:
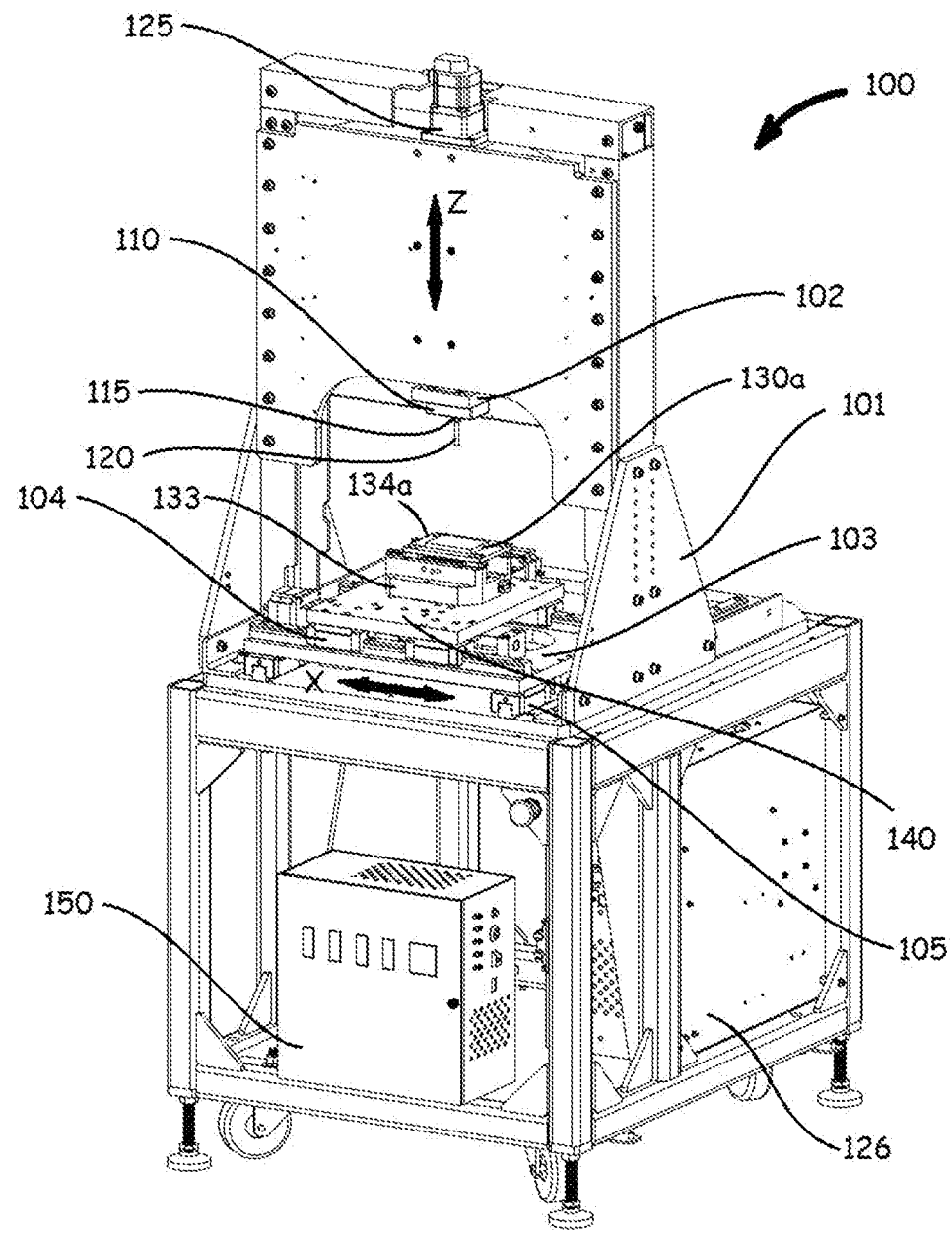
FIG. 2 is a three-dimensional view of the tester of the present invention.

Referring to the figures, wherein like parts are designated with like numerals and symbols, a universal mechanical tester of the invention, which in its entity is designated by reference numeral 100, is shown in FIG. 2, which is a three-dimensional view of the tester. The tester comprises: a frame 101, that supports a carriage 102 moveable in a vertical plane in the direction indicated by arrow Z, the frame having a base; and a positioning stage 103, which is movably installed on the base of the frame and moveable in a horizontal plane. The positioning stage comprises at least one slide 104 movable in one direction indicated by arrow X. The slide supports a platform 140, which is movable along with the slide.

Figure 3:
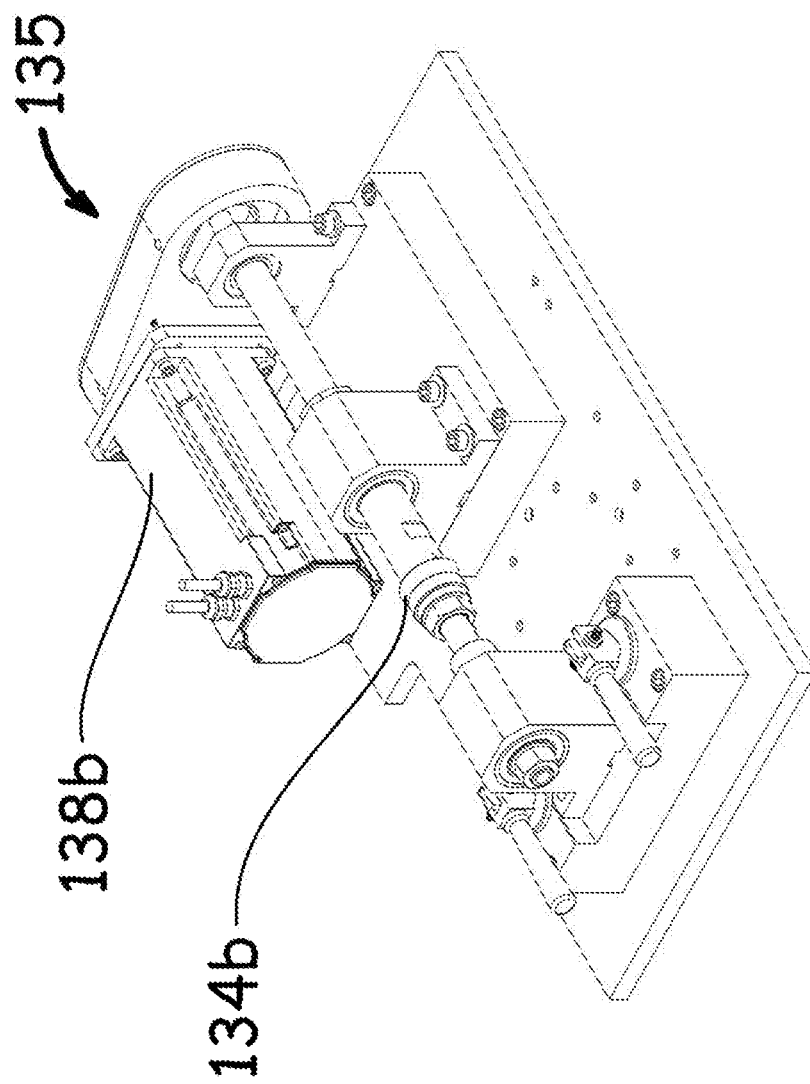
FIG. 3 is a three-dimensional view of a lower sample stage of the present invention with rotational motion around a horizontal axis.
Figure 4:
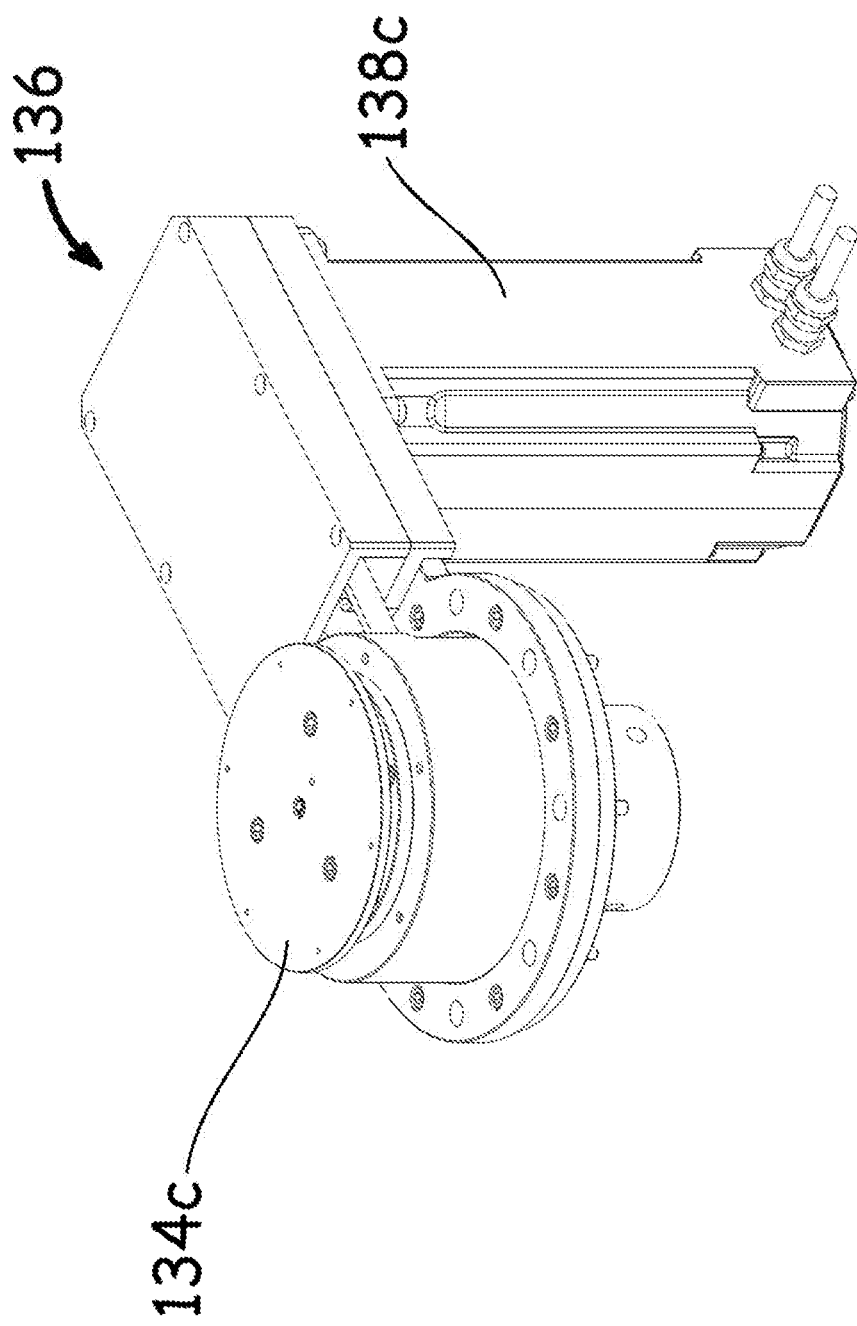
FIG. 4 is a three-dimensional view of a lower sample stage of the present invention with rotational motion around a vertical axis.
Figure 5:
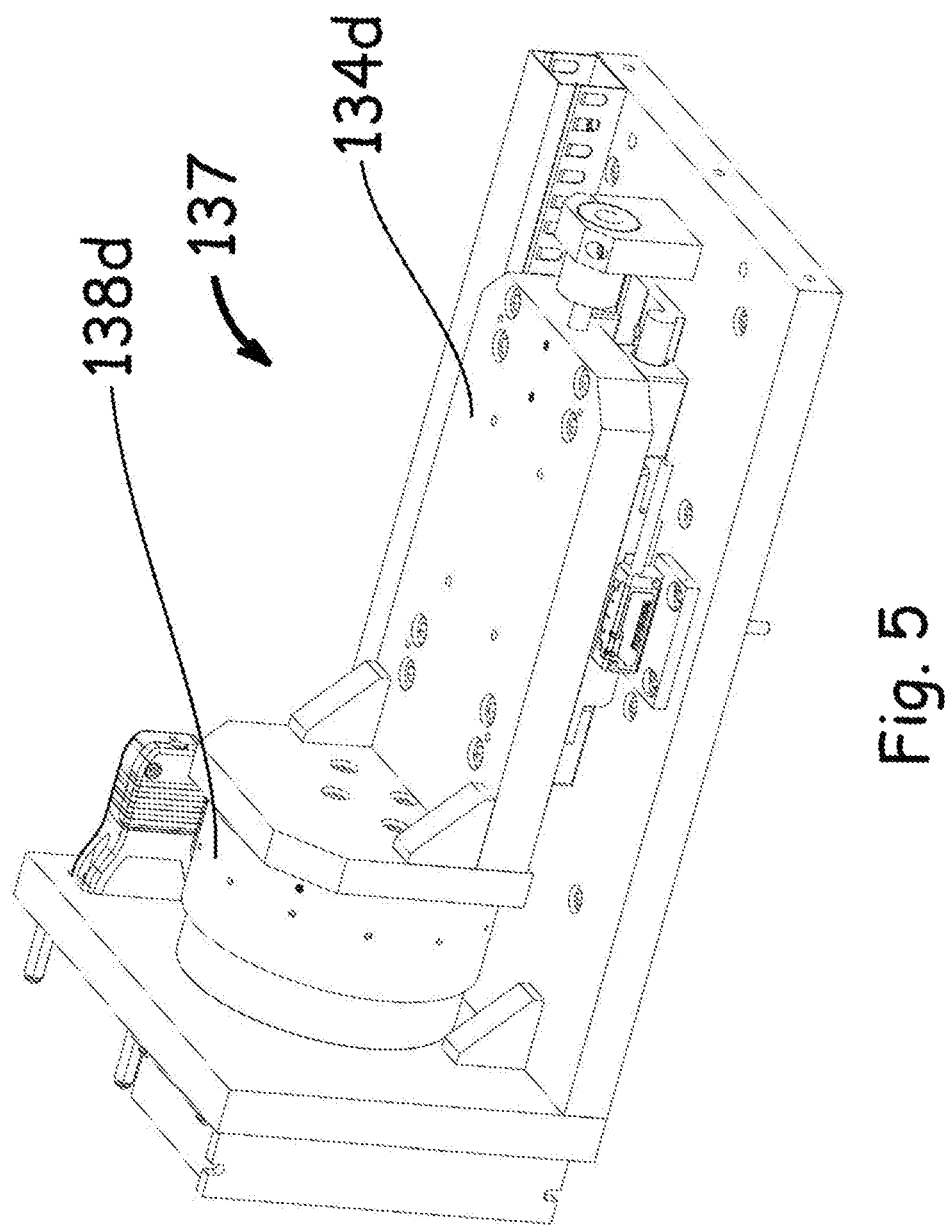
FIG. 5 is a three-dimensional view of a lower sample stage of the present invention with fast-oscillating motion in a horizontal plane.

A force sensor assembly 110 for measuring applied forces is attached to the carriage and can be moved in the vertical direction; a holder 115 for an upper specimen 120 is connected to the force sensor assembly; a carriage moving mechanism 125 controlled by an electronic programmable motion control module 126 moves the carriage in the vertical direction and thus causes the upper specimen to exert a predetermined force on a lower specimen 130a. In FIG. 2, one of the modular sample stages is represented by a linearly reciprocating stage 133. Each of the modular sample stages includes a support (134a in FIG. 2) for the lower specimen and a driving mechanism for moving the lower specimen relative to the upper specimen (not shown in FIG. 2). The modular sample stage can perform linear reciprocation in a horizontal direction, e.g., in the direction shown by arrow X in FIG. 2, or rotation around a horizontal axis, as in a "Block-on-Ring" sample stage 135 (FIG. 3), or rotation around a vertical axis, as in a rotary stage 136 (FIG. 4), or fast oscillation in a horizontal plane, as in a "Fretting" stage 137 (FIG. 5), or unidirectional sliding in a horizontal direction. Each modular sample stage includes an actuator 138 (which in FIG. 3 corresponds to the actuator 138b; in FIG. 4—to the actuator 138c; and in FIG. 5—to the actuator 138d) optimized for a specific test to be performed on the sample stage. In this connection, an appropriate actuator may comprise a motor, as shown in FIG. 3 and FIG. 4, an electro-magnetic device (e.g., a voice coil), as shown in FIG. 5, a piezo-electric device, a hydraulic oscillator, or a device of any other type suitable for the test operation. The modular sample stages are interchangeably connected to and supported by the platform 140 (FIG. 2), which is supported by the slide 104 of the positioning stage 103 and allows repositioning of the modular sample stage with the lower sample relative to the upper specimen. Therefore, a normal load can be applied from the upper specimen to the lower sample at any point within the range of motions of the positioning stage, while the force sensor assembly remains centered relative to the carriage. As a result, the carriage moving mechanism is not subject to an off-center loading. This, in turn, allows to improve reliability and increase load capacity of the carriage and the carriage moving mechanism. It is understood that for expanding the range of motions the positioning stage 103 may be provided with a second slide 105 moveable in a horizontal plane in a direction perpendicular to the direction shown by arrow X.

Operation of the universal mechanical tester of the invention and execution of the desired test procedures are controlled by a central processing unit (CPU) 150 according to predetermined test protocols. According to one or several aspects of the invention, the tester is a machine capable of accepting modular sample stages that automatically activate only those test protocols which are appropriate for the particular modules installed in the instrument. Each replaceable modular sample stage is equipped with an identifier defined herein as a set of means for automatically identifying a modular sample stage connected to the platform, while the frame of the tester of invention comprises a detector defined herein as a set of means for detecting and automatically recognizing the identifier in a modular sample stage attached to the platform, thus allowing the CPU to recognize the type of the installed modular sample stage (reciprocating, rotating, etc.) and to activate only the software relevant to the operation of a modular sample stage of a particular type. For example, with a rotary stage installed on the tester the CPU will allow an operator to select the speed of rotation and the radial position of the upper specimen on the lower sample relative to the center of rotation for a wear test script or for a friction measurement, but it will not allow activation of any software or test protocol intended for use with another modular sample stage (such as for tests requiring fast linear oscillation of the sample).

According to one or several aspects of the invention, this can be achieved by providing a modular sample stage with an electronic identification device linked with a first set of electrical contacts, arranged, for example, in a connector mounted on the modular sample stage or on a cable, which is connected to the stage actuator; providing the tester frame with a second set of electrical contacts arranged, for example, in a signal or power supply connector and linked with the CPU, wherein the first set of electrical contacts mating with the second set of electrical contacts; and programming the CPU with a set of commands allowing the CPU to automatically detect the presence of a modular sample stage and to recognize the stage parameters without any operator's intervention.

Figure 6:
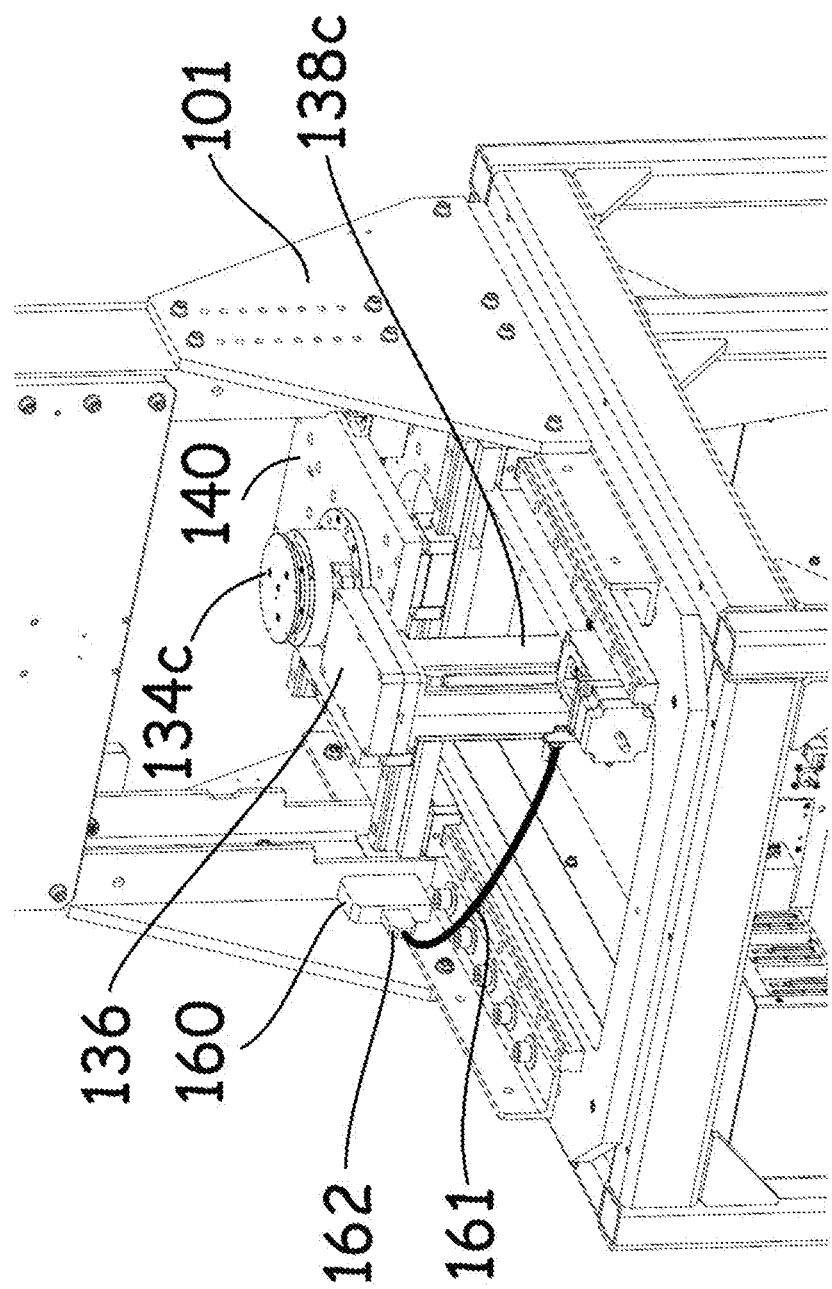
FIG. 6 is a partial three-dimensional rear view of the tester of the invention with a rotary stage installed on the platform.

The electronic identification device or identifier can include active semiconductor components, for example an EPROM chip, such as AT24C by Atmel Corp., with pre-programmed set of modular sample stage parameters, or an IC chip with a pre-programmed serial number, such as DS2401 by Maxim Integrated, or passive components like a DIP switch having a certain combination of closed and open contacts, or just a number of jumpers and shunts interconnecting the contacts in the modular sample stage connector and thus providing for a recognizable wiring pattern, or other means known to those skilled in the art. This aspect of the invention is illustrated in FIG. 6, which is a partial three-dimensional rear view of the tester of invention with a rotary stage 136 installed on the platform 140. The motor 138c of the rotary stage is connected to the tester by a control cable 161 with a connector 162, which has electrical contacts dedicated for a motor control and also comprises the first set of electrical contacts linked to the rotary stage electronic identification device (not seen). The frame 101 of the tester is provided with a detecting module 160 comprising a connector with electrical contacts linked to the electronic programmable motion control module (not seen) for the motor control and with the second set of electrical contacts linked to the CPU for the detection of the sample stage. When a stage is installed on the platform, the connector 162 on the motor cable 161 is plugged into the mating connector on the detecting module 160, and the first set of electrical contacts linked with the stage electronic identification device engage and mate with the second set of electrical contacts in the detecting module, whereby the stage electronic identification device is getting connected to the tester CPU, which executes a set of commands to detect the presence and a status of the electronic identification device, thus automatically identifying the attached modular sample stage and enabling a set of test protocols or test operations relevant only to the attached stage. It is understood that the electronic identification device can be mounted on the motor, or on the stage, or in the motor cable connector.

Figure 7:
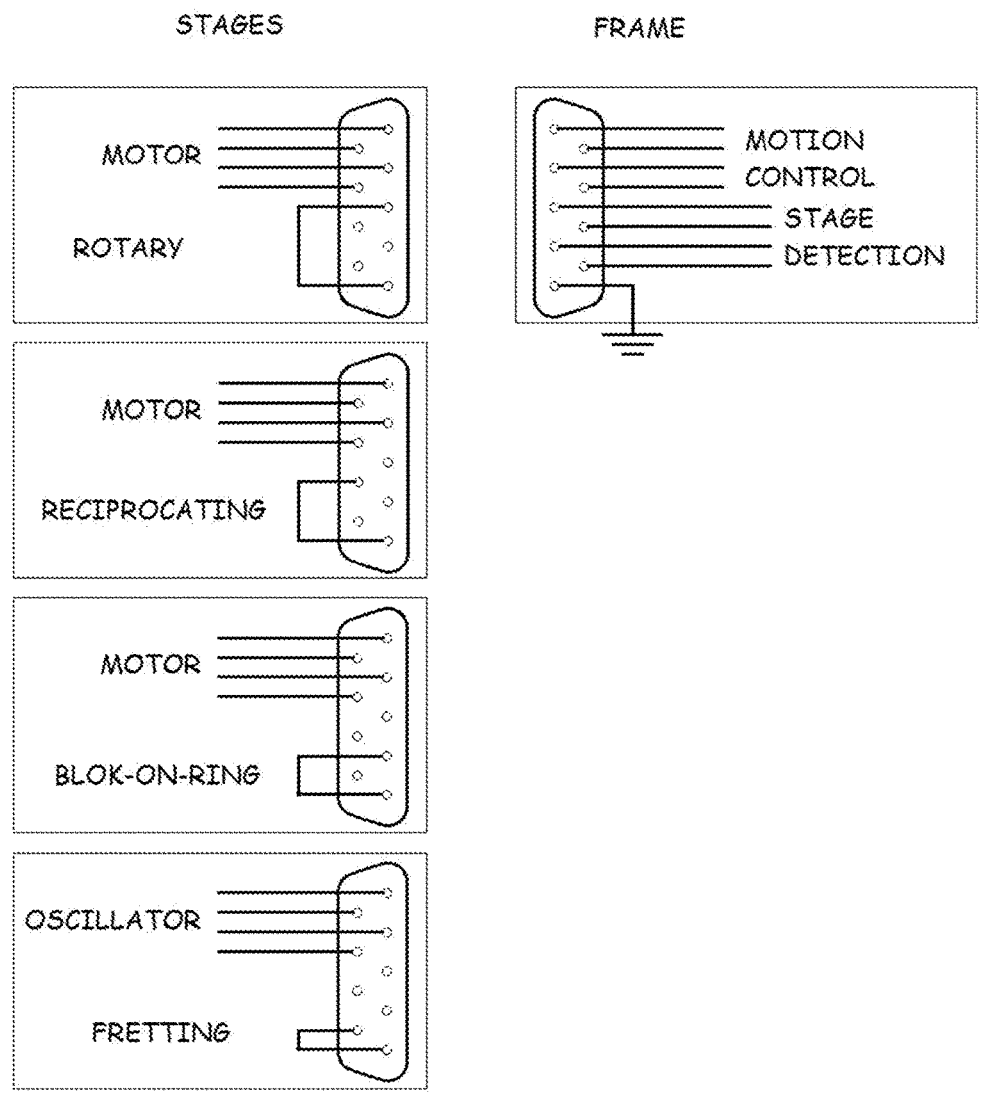
FIG. 7 is an example of a wiring diagram for a sample stage automatic identification.

FIG. 7 illustrates an example of one of the simplest possible implementations of the electronic identification device based on a set of jumpers inside the motor connector. Depending on the position of a jumper connecting two contacts in the connector on the motor cable the CPU can recognize a modular sample stage installed on the platform and connected to the tester.

Figure 8:
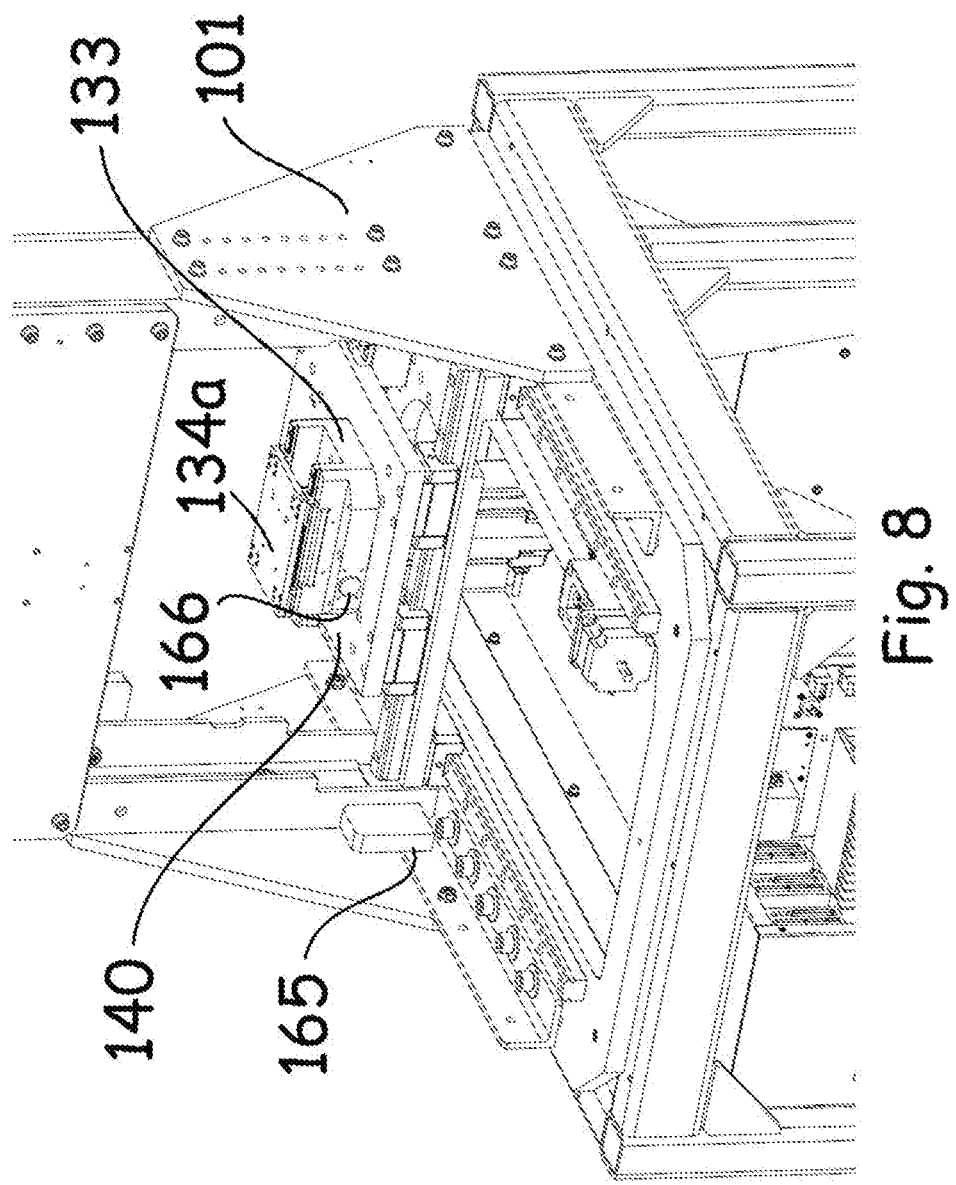
FIG. 8 is a partial three-dimensional rear view of the tester of the invention with a reciprocating stage installed on the platform.

According to another aspect of the invention, the set of means for automatically identifying a modular sample stage comprises a wireless electronic identification device or identifier, either active or passive, linked with a modular sample stage and a wireless receiving device or a wireless detector coupled to the tester frame and linked to the CPU, which executes a set of commands to detect the presence and a status of the wireless electronic identification device, thus automatically identifying the attached modular sample stage and enabling a set of test protocols relevant only to the attached stage. The wireless identifier can include passive components, such as RFID chips, tags, and labels, for example LXMS31AC by Murata Electronics or MN63Y3212 by Panasonic, or active semiconductor components, such as active RFID tags, for example ATA6286 by Atmel Corp., with a pre-programmed set of stage parameters. The wireless detector can include a RF transmitter and receiver, such as RI-STU-MRD2 by Texas Instruments or DLP-RFID1 module by DLP Design, or other means known to those skilled in the art. This aspect of the invention is illustrated in FIG. 8, which is a partial three-dimensional rear view of the tester of invention with a reciprocating stage 133 having a wireless electronic identification device 166 and installed on the platform 140. The frame 101 of the tester is provided with a wireless detector 165 linked to the CPU for the sample stage detection. When the modular sample stage is installed on the platform, the wireless electronic identification device is within a working distance from the wireless receiving device, which detects the presence of the wireless electronic identification device, retrieves the information stored in it, and allows the CPU to execute a set of commands to recognize and identify the attached modular sample stage and to enable a set of test protocols or test operations relevant only to the attached stage.

According to yet another aspect of the invention, each of the alternative force sensor assemblies includes an identifier—a set of means for identifying a sensor assembly attached to the carriage. The tester is equipped with a detector, which constitutes a set of means for detecting and recognizing a force sensor assembly attached to the carriage and which is linked to the tester CPU that executes a pre-programmed set of commands for detecting the presence and automatically identifies the installed force sensor, retrieves information regarding the sensor configuration (such as a working load range, calibration characteristics, etc.) and enables a set of test protocols or test operations relevant only to the attached force sensor assembly. For example, by identifying the installed force sensor and defining its maximum load range, the CPU will allow an operator to select the applied normal load for a wear test script or for a friction measurement only within the defined range and will automatically set safety limits for the load and the friction force in the test protocol, but it will not allow activation of any software or test protocol for a load exceeding the working range or a safe limit. Also, by retrieving the calibration characteristics of the attached force sensors, the CPU will automatically implement correction factors for measurement of the force, thus improving the measurement accuracy.

According to another aspect of the invention, a set of means for identifying a force sensor comprises: an identifier attached to the sensor and linked with a first set of electrical contacts; a detector coupled to the frame of the tester and having a second set of electrical contacts, which are linked to the CPU, wherein the first set of electrical contacts mating and engages with the second set of electrical contacts when the sensor is mounted on the carriage and connected to the tester; and a set of commands pre-programmed in the CPU, which allow the CPU to automatically detect the presence of a force sensor on the carriage, to recognize the sensor parameters without any operator's intervention, and to automatically enable only those test operations and protocols that correspond to the sensor attached to the carriage.

According to yet another aspect of the invention, a set of means for identifying a force sensor comprises a wireless identifier coupled with the sensor, a wireless detector coupled to the frame and linked to the CPU, and a set of commands pre-programmed in the CPU, which allow the CPU to automatically detect the presence of a force sensor on the carriage, recognize sensor parameters without any operator's intervention, and automatically enable only test operations and protocols corresponding to the sensor installed on the carriage.

According to yet another aspect of the invention, a set of means for identifying a force sensor assembly further comprises a memory module coupled to the force sensor assembly for storing a set of characteristics of the force sensor assembly such as the sensor calibration coefficients or a look-up table and a microcontroller module coupled to the force sensor assembly for retrieving and processing the set of characteristics of the force sensor assembly stored in the memory module, and for communicating with the tester CPU. The memory module and the microcontroller module can be combined into one unit, such as, for example, LPC1315/16/17/45/46/47 by NXP Semiconductors.

The tester of the invention further provides means for performing tests at various environmental conditions, in particular at elevated or lower temperatures, in an atmosphere with controlled humidity and/or gas composition, in vacuum, in a liquid, etc. A number of environment chambers programmably controlled by the CPU can be removably and interchangeably attached to a modular sample stage, the platform, or the frame of the tester of the present invention.

According to one or several aspects of the invention, the tester of the invention further provides a set of means for identifying an environment chamber coupled to the modular sample stage and for automatically enabling only those test operations and test protocols that correspond to the environment chamber coupled to the modular sample stage. Similar to the set of means for identifying a modular sample stage or a force sensor assembly, a set of means for identifying an environment chamber comprises an identifier coupled to a chamber and a detector coupled to the tester frame and linked to the CPU. Upon placing the chamber on a respective modular sample stage, the detector automatically detects the identifier on the environment chamber and couples it with the CPU. The CPU executes a pre-programmed set of commands to recognize the environment chamber and its parameters and automatically enables only those test operations and test protocols that correspond to the environment chamber coupled to the modular sample stage. For example, if a heating chamber with the temperature limit of 500 degrees is installed on the sample stage, the CPU will not allow the operator to set the test temperature above this limit and will not enable a test protocol related to a humidity chamber.

Figure 9:
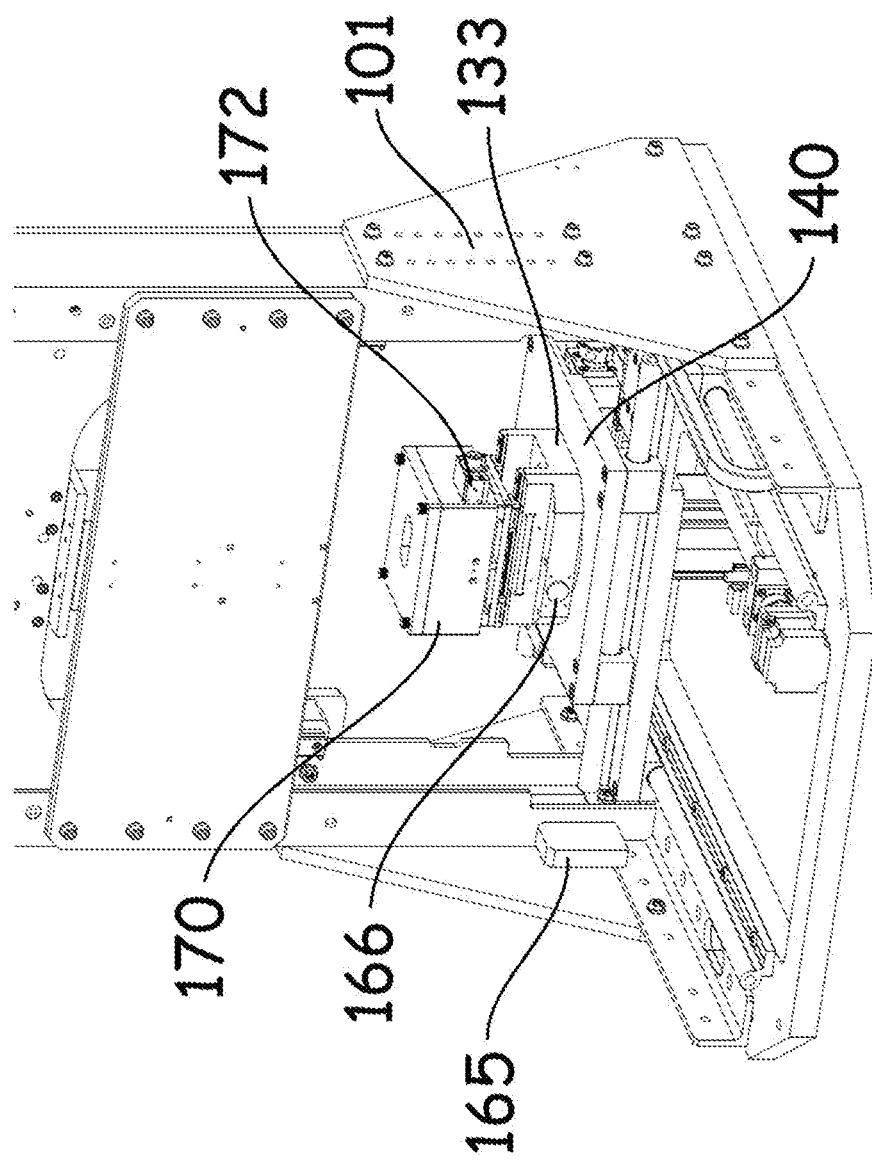
FIG. 9 is a partial three-dimensional rear view of the tester of the invention with a reciprocating stage installed on the platform and an environment chamber mounted on the reciprocating stage.

This aspect of the invention is illustrated in FIG. 9, which is a partial three-dimensional rear view of the tester of invention with a reciprocating stage 133 installed on the platform 140. The stage electronic identification device 166 is coupled with the detector 165 mounted on the frame 101 and connected to the CPU for identification of the sample stage as was described earlier. An environment chamber 170 controlled by the tester CPU is mounted on the reciprocating stage and equipped with an identifier 172. When the environment chamber is placed on the platform and connected to the tester, the identifier is automatically coupled with the detector, which allows the CPU to recognize and identify the attached environment chamber and to enable a set of test protocols or operations relevant only to the attached chamber.

According to another aspect of the invention, a set of means for identifying an environment chamber comprises: an identifier attached to the chamber and linked with a first set of electrical contacts; a detector attached to the frame of the tester and having a second set of electrical contacts, which are linked to the CPU, wherein the first set of electrical contacts mating and engages with the second set of electrical contacts when the environment chamber is installed on the corresponding modular sample stage; and a set of commands pre-programmed in the CPU so that the CPU can automatically detect the presence of an environment chamber on the modular sample stage, recognize the environment chamber parameters without any operator's intervention, and automatically enable only those test operations and protocols that correspond to the environment chamber installed on the modular sample stage.

According to yet another aspect of the invention, a set of means for identifying an environment chamber comprises: a wireless identifier attached to the chamber; a wireless detector attached to the frame of the tester and linked to the CPU; and a set of commands pre-programmed in the CPU, which allow the CPU to automatically detect an environment chamber on the modular sample stage and to recognize the environment chamber parameters without any operator's intervention, and to automatically enable only those test operations and protocols that correspond to the environment chamber installed on the modular sample stage.

The tester of the invention further provides a monitor module for sensing and monitoring the environmental conditions during the test operations. The monitor module comprises sensors for monitoring temperature of the lower and of the upper samples, for monitoring temperature in the environment chambers, and for monitoring humidity in the environment containing the samples.

The tester of the invention further provides a control and measurement module for controlling and measuring test parameters during the test operations. The control and measurement module comprises: means for controlling and measuring voltage and current applied to the upper and lower specimens; means for controlling and measuring electrical resistance across the upper and lower specimens; and means for measuring acoustic emission on the upper and lower specimens.

It is understood that each of the sensors for sensing and monitoring the temperature and the humidity and means for measuring and controlling the voltage, the current, the resistance, and the acoustic emission can be equipped with a set of means for automatic identification similar to the set of means for identifying a modular sample stage connected to the platform, and can be connected either via mating contacts or wirelessly to the CPU programmed for executing a predetermined set of test operations and automatically enabling only those test operations and protocols that are relevant to the sensors and means that are coupled to the tester and identified by the CPU.

It is further understood that the tester CPU can be linked to at least one external peripheral unit, such as a monitor, a human interface device (keyboard, mouse, touchpad, trackball, etc.), an external central processor unit, a data storage unit, a network interface device, a printer, etc., for storing, processing, analyzing, and presenting a set of data obtained during the test operations. The tester of the invention is further provided with a linking interface device for linking the tester CPU to an external peripheral unit; this linking interface device being selected from a plurality of interface devices comprising wired or wireless interface devices.

Thus, the proposed universal mechanical tester for measuring friction and wear characteristics of materials enables all types of test configurations on a single machine equipped with multiple sample stage modules and sensors, each adapted and optimized for a particular type of test protocol.

It is preferred that any data obtained by calibration of tester components be saved within the electronics of the respective component. This allows the component to be plugged into a new tester and be readily identified with its calibration parameters so the tester can be used correctly without further calibration. It is also preferred that the data acquisition and motor control electronics be placed within the housing of the tester. This minimizes the number of electronic connections between the CPU and the tester. It is understood that the CPU programmed for identifying the modules currently installed in the tester, executing a corresponding predetermined set of test operations, and controlling the various functions of the tester is preferably housed within the frame of the tester 101.

Thus, the above-described new universal mechanical tester for measuring friction and wear characteristics of materials provides the following improvements:
- a quicker change between test configurations;
- a lower sample positioning stage with sliders and platform having larger motion range, not limited by the carriage space and capable to accommodate various modular sample stages;
- a greater number of modular sample stages with variety of motions and actuators not limited by a single motor fixed to the frame of the tester and with actuators optimized for specific test operations;
- an improved loading stage comprising a vertical carriage and a force sensor mounted at the center of the carriage, not susceptible to off-center loading and parasitic moments, and thus having higher load capacity and improved reliability; and
- automatic hardware identification that allows the software to adapt to the tester configuration that shows the operator only the information relevant to that particular tester configuration.

References throughout this specification that may have been made to 'one embodiment,' 'an embodiment,' 'a related embodiment,' or similar language mean that a particular feature, structure, or characteristic described in connection with the referred to 'embodiment' is included in at least one embodiment of the present invention. Thus, appearances of the phrases 'in one embodiment,' 'in an embodiment,' and similar language throughout this specification may, but do not necessarily, all refer to the same implementation of the invention. It is to be understood that no portion of disclosure, taken on its own and in possible connection with a figure, is intended to provide a complete description of all features of the invention.

In addition, it is to be understood that no single drawing is intended to support a complete description of all features of the invention. In other words, a given drawing is generally descriptive of only some, and generally not all, features of the invention. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

While the invention has been shown and described herein with reference to what are believed to be the most practical embodiments, it is recognized that departures can be made within the scope of the invention and, therefore, the invention is not to be limited to the details disclosed herein but is to be accorded the full scope of equivalent articles.

What we claim is:

1. A universal mechanical tester for measuring friction and wear characteristics of materials, comprising:
    a frame with a base, wherein the frame supports a carriage moveable in a vertical direction;
    a positioning stage, which is movably installed on the base and moveable in a horizontal plane, the positioning stage comprises at least one slide movable in one direction and supporting a platform, which is movable along with the slide;
    a force sensor assembly attached to the carriage;
    a holder for holding an upper specimen, the holder being connected to the force sensor assembly;
    a plurality of modular sample stages interchangeably connectable to the platform of the positioning stage, each modular sample stage having a support for a lower specimen and a driving mechanism for moving the lower specimen relative to the upper specimen, the driving mechanism being selected from the group consisting of a rotary driving mechanism for rotation around a vertical axis, a rotary driving mechanism for rotation around a horizontal axis, and a linear driving mechanism for reciprocating in a horizontal direction;
    a carriage moving mechanism for engaging the upper specimen and the lower specimen and for applying a predetermined force from the upper specimen to the lower specimen;
    a set of electronic identification devices for identifying a modular sample stage connected to the platform;
    an electronic programmable motion control module for moving the positioning stage and the carriage and for varying the force applied from the upper specimen to the lower specimen; and
    a central processing unit (CPU) programmed for executing a set of predetermined test operations, wherein the set of predetermined test operations comprises subsets of test operations associated with the modular sample stages connected to the platform and identified by the electronic identification device; the CPU being preprogrammed for automatically enabling only a subset of the test operations corresponding to the modular sample stage connected to the platform.

2. The apparatus according to claim 1, wherein said positioning stage comprising two slides movable in two mutually perpendicular directions.

3. The apparatus according to claim 1, wherein the set of identification units for identifying a modular sample stage connected to the platform comprises: a first set of electrical contacts linked with the modular sample stage; a second set of electrical contacts linked with the CPU, wherein the first set of electrical contacts mating with the second set of electrical contacts; and a set of commands executable by the CPU for identifying the modular sample stage.

4. The apparatus according to claim 1, wherein the set of electronic identification devices for identifying a modular sample stage connected to the platform comprises: a set of means for non-contact identification linked with the modular sample stage; a set of means for detecting said means for non-contact identification linked with the CPU; and a set of commands executable by the CPU for identifying the modular sample stage.

5. The apparatus according to claim 1, further comprising a set of means for identifying a force sensor assembly attached to the carriage and for automatically enabling only a subset of the test operations, which corresponds to the force sensor assembly attached to the carriage.

6. The apparatus according to claim 5, wherein the set of means for identifying a force sensor assembly comprises: a first set of electrical contacts linked with the force sensor assembly; a second set of electrical contacts linked with the CPU, wherein the first set of electrical contacts mating with the second set of electrical contacts; and a set of commands executable by the CPU for identifying the force sensor assembly.

7. The apparatus according to claim 5, wherein the set of means for identifying a force sensor assembly comprises: a set of means for non-contact identification linked with the force sensor assembly; a set of means for detecting said means for non-contact identification linked with the CPU; and a set of commands executable by the CPU for identifying the force sensor assembly.

8. The apparatus according to claim 5, wherein the set of means for identifying a force sensor assembly further comprises: a memory module linked with the force sensor assembly for storing a set of characteristics of the force sensor assembly; and a microcontroller module linked with the force sensor assembly for retrieving and processing said set of characteristics of the force sensor assembly.

9. The apparatus according to claim 1, further comprising an environment chamber coupled to one of said plurality of modular sample stages.

10. The apparatus according to claim 9, further comprising a set of means for identifying an environment chamber coupled to the modular sample stage and for automatically enabling only the subset of the test operations, which corresponds to the environment chamber coupled to the modular sample stage.

11. The apparatus according to claim 10, wherein the set of means for identifying an environment chamber coupled to the modular sample stage comprises: a first set of electrical contacts linked with the environment chamber; a second set of electrical contacts linked with the CPU, wherein the first set of electrical contacts mating with the second set of electrical contacts; and a set of commands executable by the CPU for identifying the environment chamber.

12. The apparatus according to claim 10, wherein the set of means for identifying an environment chamber comprises: a set of means for non-contact identification linked with the environment chamber; a set of means for detecting said means for non-contact identification linked with the CPU; and a set of commands executable by the CPU for identifying the environment chamber.

13. The apparatus according to claim 1, further comprising a monitor module for detecting and monitoring a set of environmental conditions during the test operations, wherein the monitor module is selected from the group consisting of an upper specimen temperature sensor, a lower specimen temperature sensor, an environment chamber temperature sensor, and a humidity sensor.

14. The apparatus according to claim 13, further comprising a set of means for identifying the monitor module and for automatically activating the test operations relevant to the identified monitor module.

15. The apparatus according to claim 1, further comprising a control and measurement module for controlling and measuring a set of test parameters during the test operations, wherein the control and measurement module is selected from the group consisting of a unit for controlling and measuring a voltage and a current applied to the upper and lower specimens, a unit for measuring a resistance across the upper and lower specimens, and a unit for measuring an acoustic emission on the upper and lower specimens.

16. The apparatus according to claim 15, further comprising a set of means for identifying the control and measurement module and for automatically activating the test operations relevant to the identified control and measurement module.

17. The apparatus according to claim 1, wherein the linear driving mechanism for reciprocating in a horizontal direction is selected from the group consisting of a linear electromagnetic actuator, a piezo-electric actuator, and a hydraulic linear actuator.

* * * * *